US009903792B2

(12) United States Patent
Magin et al.

(10) Patent No.: US 9,903,792 B2
(45) Date of Patent: Feb. 27, 2018

(54) VENTILATOR-ENDOTRACHEAL TUBE-LUNG BENCHTOP MODEL

(71) Applicant: SHARKLET TECHNOLOGIES, INC., Aurora, CO (US)

(72) Inventors: Chelsea Marie Magin, Denver, CO (US); Shravanthi T. Reddy, Goleta, CA (US); Rhea Marie May, Morrison, CO (US); Michael Ryan Mettetal, Denver, CO (US); MiKayla Maye Henry, Golden, CO (US)

(73) Assignee: SHARKLET TECHNOLOGIES, INC., Aurora, CO (US)

( * ) Notice: Subject to any disclaimer, the term of this patent is extended or adjusted under 35 U.S.C. 154(b) by 105 days.

(21) Appl. No.: 14/926,535

(22) Filed: Oct. 29, 2015

(65) Prior Publication Data

US 2016/0123846 A1 May 5, 2016

Related U.S. Application Data

(60) Provisional application No. 62/072,657, filed on Oct. 30, 2014.

(51) Int. Cl.
*A61M 16/04* (2006.01)
*G01M 99/00* (2011.01)

(52) U.S. Cl.
CPC .......... *G01M 99/008* (2013.01); *A61M 16/04* (2013.01); *A61M 16/0434* (2013.01); *A61M 2205/70* (2013.01)

(58) Field of Classification Search
CPC ................ G01M 99/008; A61M 16/04; A61M 16/0434; A61M 2205/70
USPC .............................................................. 73/37
See application file for complete search history.

(56) References Cited

U.S. PATENT DOCUMENTS

| 5,584,701 A * | 12/1996 | Lampotang | A61B 5/1106 434/262 |
| 5,772,442 A * | 6/1998 | Lampotang | G09B 23/285 434/262 |
| 6,910,896 B1 * | 6/2005 | Owens | G09B 23/288 434/267 |
| 2004/0110117 A1 * | 6/2004 | van Oostrom | G09B 23/30 434/262 |

* cited by examiner

*Primary Examiner* — Natalie Huls
*Assistant Examiner* — Monica S Young
(74) *Attorney, Agent, or Firm* — Cantor Colburn LLP

(57) ABSTRACT

Disclosed herein is a ventilator text fixture comprising a ventilator port that connects to a ventilator through a breathing circuit; where the ventilator delivers air through the ventilator port to a ventilator test fixture at a rate and pressure that can be controlled by a user to simulate inhalation; an input port; where the input port is in fluid communication with the ventilator port; where the input port permits additional simulated secretions or test liquids to be pumped into the ventilator text fixture; one or more bent supports; a liquid reservoir; where the liquid reservoir is operative to hold test fluids; and one or more tubes; where the one or more tubes are in fluid communication with the ventilator port and the input port via the liquid reservoir; and where the one or more bent supports are operative to mimic an anatomy of the trachea.

6 Claims, 2 Drawing Sheets

VENTILATOR-ENDOTRACHEAL TUBE-LUNG BENCHTOP MODEL

BACKGROUND

This disclosure relates to a benchtop model for a ventilator-endotracheal tube lung.

Endotracheal intubation disrupts the physiological homeostasis of respiratory system secretion (e.g., mucus) production and clearance. Airway secretions consequently accumulate inside the endotracheal tube lumen causing partial obstruction. Luminal narrowing is a common result of secretion accumulation and correlates with increased airflow resistance and increased endotracheal tube related work of breathing for the patient. Complete occlusion of the endotracheal tube can occur abruptly after secretion accumulation resulting in a life-threatening lack of airflow and requiring emergency intervention. The development of pre-clinical benchtop models to validate feasibility of novel tube designs to inhibit luminal occlusion are therefore a useful step prior to animal and clinical trials.

SUMMARY OF THE INVENTION

Disclosed herein is a ventilator text fixture comprising a ventilator port that connects to a ventilator through a breathing circuit; where the ventilator delivers air through the ventilator port to a ventilator test fixture at a rate and pressure that can be controlled by a user to simulate inhalation; an input port; where the input port is in fluid communication with the ventilator port; where the input port permits additional simulated secretions or test liquids to be pumped into the ventilator text fixture; one or more bent supports; a liquid reservoir; where the liquid reservoir is operative to hold test fluids; and one or more tubes; where the one or more tubes are in fluid communication with the ventilator port and the input port via the liquid reservoir; and where the one or more bent supports are operative to mimic an anatomy of the trachea.

Disclosed herein is a method of manufacturing a ventilator text fixture comprising disposing a tube in a sealed reservoir that holds test fluids; where the tube is bent in a manner so as to be operative to mimic an anatomy of the trachea; where one end of the tube contacts an air splitter while the opposing end of the tube is in fluid communication with the sealed reservoir; and disposing an input port on a periphery of the sealed reservoir; where the input port permits additional simulated secretions or test liquids to be pumped into the ventilator text fixture. The bench top model is used for investigation of interaction of airway secretions with airway management devices such as endotracheal tubes during ventilation.

DETAILED DESCRIPTION

Figure 1:
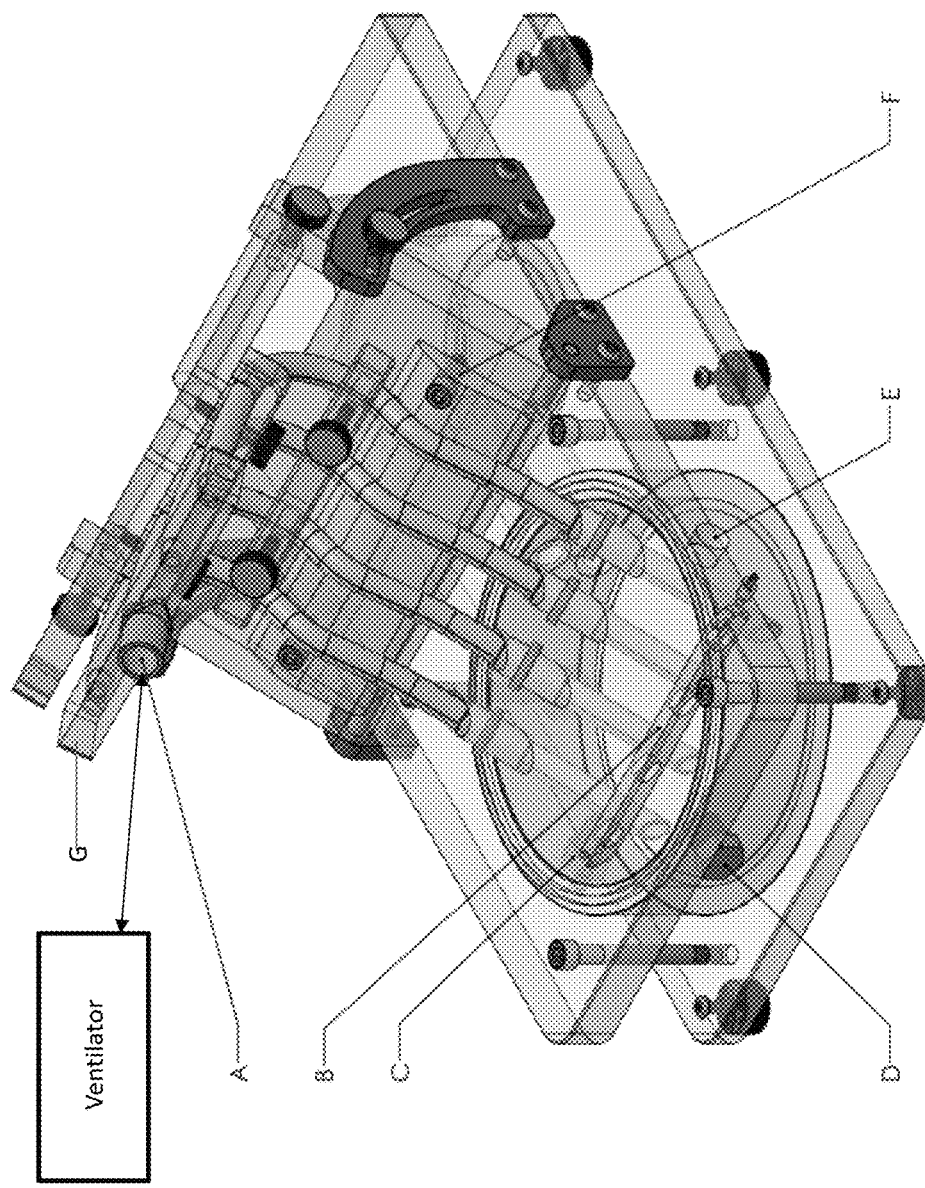
FIG. 1 is an isometric view of the ventilator test fixture.
Figure 2:
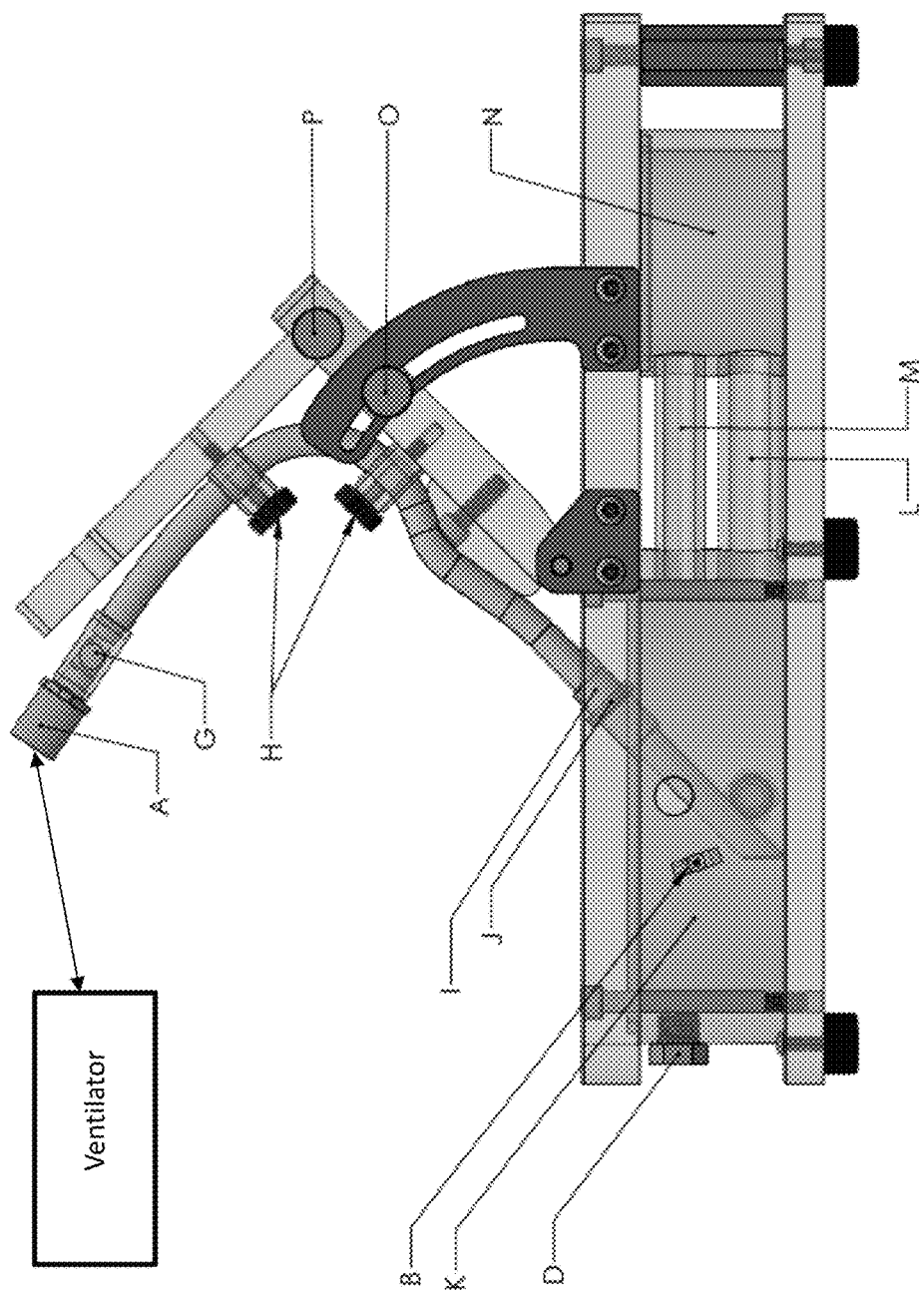
FIG. 2 is a side view of the ventilator test fixture.

Disclosed herein is a benchtop model for a ventilator-endotracheal tube lung. FIGS. 1 and 2 show a model. Tables 1 and 2 detail the parts shown in the FIGS. 1 and 2 respectively. FIG. 1 is an isometric view of the benchtop model while FIG. 2 is a side view of the same model.

TABLE 1

| Label | Part Name | Description |
|---|---|---|
| A | Ventilator Port | Port that connects to a medical ventilator through a standard breathing circuit. The ventilator delivers air through this port to the ventilator test fixture at a rate and pressure that can be controlled by the user to simulate ventilation. |
| B | Tube Tip Holder | Adjustable holder for precise placement of endotracheal tube tips within the test fixture. Tube tips are inserted into the holder and the holder is adjusted by rotation to align tube tips. |
| C | Drain Port | Port that allows simulated secretions or other test liquids to be drained from the test fixture. |
| D | Input Port | Port that allows additional simulated secretions or test liquids to be pumped into the text fixture. |
| E | Test Lung Port | Port that attaches to a test lung, which returns air delivered through the ventilator to the ventilator test fixture to simulate exhalation. |
| F | Support for Anatomical Tracheal Bending (bent support) | This support creates a bend in the test specimen (e.g. endotracheal tube) that mimics the anatomy of the trachea. |

TABLE 2

| Label | Part Name | Description |
|---|---|---|
| A | Ventilator Port | Port that connects to a medical ventilator through a standard breathing circuit. The ventilator delivers air through this port to the ventilator test fixture at a rate and pressure that can be controlled by the user to simulate inhalation. |
| B | Tube Tip Holder | Adjustable holder for precise placement of endotracheal tube tips within the test fixture. Tube tips are inserted into the holder and the holder is adjusted by rotation to align tube tips. |
| D | Input Port | Port that allows additional simulated secretions or test liquids to be pumped into the text fixture. |
| G | Air Splitter | This device divides airflow from the ventilator into several tube samples. In this example, four tubes are connected to the splitter. |
| H | Sample Holders | These holders secure four tubes in place on the test fixture and accommodate the use of supports to mimic anatomical tracheal bending. |

TABLE 2-continued

| Label | Part Name | Description |
|---|---|---|
| I | Sample Sleeves | These rigid plastic sleeves support sample tubes within the test fixture and provide a way to create an airtight seal within the fixture. |
| J | Sample Entry Points | Ports designed with recessed O-rings to allow for tubes to enter into the liquid reservoir while maintaining a consistent pressure level inside the test fixture. |
| K | Liquid Reservoir | Sealed reservoir that holds test fluids. |
| L | Liquid Bridge | Connects the main liquid reservoir to the sensor reservoir for liquid level monitoring and maintenance. |
| M | Air Bridge | Connects the main liquid reservoir to the sensor reservoir to maintain pressure equilibrium within the fixture. |
| N | Sensor Reservoir | This reservoir provides an access point for a liquid level sensor (e.g., a float sensor, a conductivity sensor or an ultrasonic sensor) that can detect when the test liquid level is low. The sensor is attached to a relay circuit that activates a pump to deliver more test liquid to the fixture via Port D. |
| O, P | Supports for Anatomical Tracheal Bending | These supports create bends that mimics the anatomy of the trachea. They are adjustable so that the user can control the angle of each bend to mimic different head of bed angles or tracheal anatomy. |

Four tubes are inserted into Sample Sleeves (I) and sealed using a thermoplastic or thermosetting material. Other viscous adhesives may also be used.

Examples of the thermoplastic polymers are polyacetals, polyolefins, polyacrylics, polycarbonates, polystyrenes, polyesters, polyamides, polyamideimides, polyarylates, polyarylsulfones, polyethersulfones, polyphenylene sulfides, polyvinyl chlorides, polysulfones, polyimides, polyetherimides, polytetrafluoroethylenes, polyetherketones, polyether etherketones, polyether ketone ketones, polybenzoxazoles, polyphthalides, polyacetals, polyanhydrides, polyvinyl ethers, polyvinyl thioethers, polyvinyl alcohols, polyvinyl ketones, polyvinyl halides, polyvinyl nitriles, polyvinyl esters, polysulfonates, polysulfides, polythioesters, polysulfones, polysulfonamides, polyureas, polyphosphazenes, polysilazanes, styrene acrylonitrile, acrylonitrile-butadiene-styrene (ABS), polyethylene terephthalate, polybutylene terephthalate, polyurethane, ethylene propylene diene rubber (EPR), polytetrafluoroethylene, perfluoroelastomers, fluorinated ethylene propylene, perfluoroalkoxyethylene, polychlorotrifluoroethylene, polyvinylidene fluoride, polysiloxanes, or the like, or a combination comprising at least one of the foregoing thermoplastic polymers.

Examples of thermosetting are epoxy polymers, unsaturated polyester polymers, polyimide polymers, bismaleimide polymers, bismaleimide triazine polymers, cyanate ester polymers, vinyl polymers, benzoxazine polymers, benzocyclobutene polymers, acrylics, alkyds, phenol-formaldehyde polymers, novolacs, resoles, melamine-formaldehyde polymers, urea-formaldehyde polymers, hydroxymethylfurans, isocyanates, diallyl phthalate, triallyl cyanurate, triallyl isocyanurate, unsaturated polyesterimides, or the like, or a combination comprising at least one of the foregoing thermosetting polymers. Epoxy polymers are preferred.

Sample sleeves (I) containing tubes are then inserted into sample entry ports (J) and stabilized with anatomical bending supports (O and P) using sample holders (H). The liquid reservoir (K) is filled with test fluid and allowed to equilibrate with the sensor reservoir (N) through the liquid bridge (L) before assembling the test fixture with screws. The test fixture reservoirs contain recessed O-rings to seal the liquid reservoir (K) and the sensor reservoir (N). The test lung is attached to liquid reservoir (K) through the test lung port (E). Tubes are then connected to the air splitter (G). The air splitter (G) is attached to the breathing circuits via the ventilator port (A), which are pushed onto the ventilator inspiratory and expiratory ports. The air supply is connected to the ventilator and turned on. airflow is adjusted to achieve optimal secretion/air movement within the tubes.

Ventilator pushes air into breathing circuits at a set speed and volume. Air travels into air splitter (G) through tubing into liquid reservoir (K). Air exits test lung port (E) and into test lung. Ventilator releases air pressure and test lung pushes air back through system bringing test fluid into test tubing. This text fixture is designed to accept additions including pressure transducers for measuring pressure within each test tube and heating to physiological temperatures via a clinical warming blanket. This fixture is designed to run for multiple days. The test liquid level is maintained through a liquid level sensor that is mounted in the sensor reservoir (N). This sensor detects low liquid levels and turns on a pump that delivers more test fluid to the liquid reservoir (K) through the input port (D) via a relay circuit.

While the invention has been described with reference to some embodiments, it will be understood by those skilled in the art that various changes may be made and equivalents may be substituted for elements thereof without departing from the scope of the invention. In addition, many modifications may be made to adapt a particular situation or material to the teachings of the invention without departing from essential scope thereof. Therefore, it is intended that the invention not be limited to the particular embodiments disclosed as the best mode contemplated for carrying out this invention, but that the invention will include all embodiments falling within the scope of the appended claims.

What is claimed is:

1. A ventilator test fixture comprising: a ventilator port adapted to connect to a ventilator; where the ventilator delivers air through the ventilator port to a ventilator test fixture at a rate and pressure that can be controlled by a user to simulate inhalation; an input port; where the input port is in fluid communication with the ventilator port; where the input port permits additional simulated secretions or test liquids to be pumped into the ventilator test fixture; one or more adjustable bent supports; a liquid reservoir comprising a test lung port and the input port; wherein the test lung port is configured to push air back through the liquid reservoir and bring test fluid into the ventilator test fixture; the liquid reservoir is operative to hold test fluids; and one or more tubes; where the one or more tubes are in fluid communication with the ventilator port and the input port via the liquid reservoir; and where the one or more bent adjustable supports are operative to mimic an anatomy of the trachea.

2. The ventilator test fixture of claim 1, further comprising a tube tip holder that is operative to position a tip of the one or more tubes in the test fixture; where tube tips are inserted into the tube tip holder and where the tube tip holder is adjusted by rotation to align the tube tips.

3. The ventilator test fixture of claim 1, further comprising a drain port that is operative to drain simulated secretions or test liquids to be drained from the test fixture.

4. The ventilator test fixture of claim 1, where the test lung port is in fluid communication with a test lung, where the test lung returns air delivered through the ventilator to the ventilator test fixture to simulate exhalation.

5. The ventilator test fixture of claim 1, further comprising a liquid level sensor with an access point to the reservoir, wherein the liquid level sensor is configured to detect a low test liquid level.

6. The ventilator test fixture of claim 5, where the sensor is attached to a relay circuit that activates a pump to deliver more test liquid to the fixture via a port.

* * * * *